United States Patent
Alam

(10) Patent No.: US 9,427,438 B2
(45) Date of Patent: *Aug. 30, 2016

(54) COMPOSITIONS AND METHODS FOR TREATING ALZHEIMER'S DISEASE

(71) Applicant: EIP Pharma, LLC, Cambridge, MA (US)

(72) Inventor: John Jahangir Alam, Cambridge, MA (US)

(73) Assignee: EIP Pharma, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/855,338

(22) Filed: Sep. 15, 2015

(65) Prior Publication Data
US 2016/0030431 A1  Feb. 4, 2016

Related U.S. Application Data

(63) Continuation of application No. 14/191,984, filed on Feb. 27, 2014, now abandoned, which is a continuation of application No. 13/467,519, filed on May 9, 2012, now Pat. No. 8,697,627.

(60) Provisional application No. 61/483,919, filed on May 9, 2011.

(51) Int. Cl.
| | | |
|---|---|---|
| *A61K 31/00* | (2006.01) | |
| *A61K 31/5025* | (2006.01) | |
| *A61K 31/519* | (2006.01) | |
| *C07D 403/12* | (2006.01) | |
| *C07D 401/14* | (2006.01) | |
| *C07D 405/14* | (2006.01) | |
| *C07D 213/82* | (2006.01) | |
| *C07D 231/40* | (2006.01) | |
| *C07D 401/04* | (2006.01) | |
| *C07D 401/12* | (2006.01) | |
| *C07D 403/04* | (2006.01) | |
| *C07D 413/04* | (2006.01) | |
| *C07D 417/04* | (2006.01) | |
| *C07D 471/04* | (2006.01) | |
| *C07D 487/04* | (2006.01) | |
| *C07D 513/04* | (2006.01) | |
| *C07D 211/16* | (2006.01) | |

(52) U.S. Cl.
CPC ......... *A61K 31/519* (2013.01); *A61K 31/5025* (2013.01); *C07D 211/16* (2013.01); *C07D 213/82* (2013.01); *C07D 231/40* (2013.01); *C07D 401/04* (2013.01); *C07D 401/12* (2013.01); *C07D 401/14* (2013.01); *C07D 403/04* (2013.01); *C07D 403/12* (2013.01); *C07D 405/14* (2013.01); *C07D 413/04* (2013.01); *C07D 417/04* (2013.01); *C07D 471/04* (2013.01); *C07D 487/04* (2013.01); *C07D 513/04* (2013.01)

(58) Field of Classification Search
None
See application file for complete search history.

(56) References Cited

U.S. PATENT DOCUMENTS

| 8,697,627 B2 | 4/2014 | Alam |
| 2005/0203111 A1 | 9/2005 | David |
| 2012/0289511 A1 | 11/2012 | Alam |
| 2014/0357638 A1 | 12/2014 | Alam |

FOREIGN PATENT DOCUMENTS

| CN | 1244867 A | 2/2000 |
| JP | 2007-528393 A | 10/2007 |
| JP | 2009-541483 A | 11/2009 |
| WO | WO-98/27098 A1 | 6/1998 |
| WO | WO-2005/091891 A2 | 10/2005 |
| WO | WO-2008/002465 A2 | 1/2008 |
| WO | WO-2012/154814 A1 | 11/2012 |

OTHER PUBLICATIONS

Kumar et al (Nature Rev 2: 717-726, 2003).*
Weisman et al (Abstract FRI0018, Eur Leag Against Rheumatism (EULAR), 2002).*
Hull et al (Curr Medicinal Chem 9: 83-88, 2002—abstract only).*
Munoz et al (Neuropharmacol 58: 561-568, Epub Dec. 4, 2009).*
Alonso, M. et al., Memory formation requires p38MAPK activity in the rat hippocampus, Neuroreport., 14(15):1989-92 (2003).
Bach et al., The Role of CNI-1493 in the Function of Primary Microglia with Respect to Amyloid-β, Journal of Alzheimer's Disease, 26:69-80 (2011).
Bacher et al., CNI-1493 inhibits Aβ production, plaque formation, and cognitive deterioration in an animal model of Alzheimer's disease, The Journal of Experimental Medicine, 205(7):1593-1599 (2008).
Bachstetter, A.D. et al., Attenuation of traumatic brain injury-induced cognitive impairment in mice by targeting increased cytokine levels with a small molecule experimental therapeutic, J. Neuroinflammation, 12:69, 9 pages (2015).
Bachstetter, A.D. et al., Early stage drug treatment that normalizes proinflammatory cytokine production attenuates synaptic dysfunction in a mouse model that exhibits age-dependent progression of Alzheimer's disease-related pathology, J. Neurosci., 32(30):10201-10 (2012).
Bachstetter, A.D. et al., The p38α MAPK regulates microglial responsiveness to diffuse traumatic brain injury, J. Neurosci., 33(14):6143-53 (2013).
Bain et al., The selectivity of protein kinase inhibitors: a further update, Biochem. J., 408:297-315 (2007).

(Continued)

*Primary Examiner* — Daniel E Kolker
*Assistant Examiner* — Aditi Dutt
(74) *Attorney, Agent, or Firm* — Choate, Hill & Stewart LLP; Robert N. Sahr; Nishat A. Shaikh

(57) ABSTRACT

The present invention provides compositions for reducing amyloid plaque burden associated with Alzheimer's disease and methods of using the same.

6 Claims, 3 Drawing Sheets

(56) References Cited

OTHER PUBLICATIONS

Bhaskar et al., Regulation of Tau Pathology by the Microglial Fractalkine Receptor, Neuron 68:19-31 (2010).
Brown et al., P38 MAP kinase inhibitors as potential therapeutics for the treatment of joint degeneration and pain associated with osteoarthritis, Journal of Inflammation, 5(22):1-8 (2008).
Chlan-Fourney, J. et al., The increased density of p38 mitogen-activated protein kinase-immunoreactive microglia in the sensorimotor cortex of aged TgCRND8 mice is associated predominantly with smaller dense-core amyloid plaques, European Journal of Neuroscience, 33(8):1433-1444 (2011).
Chopra et al., Pharmacological profile of AW-814141, a novel, potent, selective and orally active inhibitor of p38 MAP kinase, International Immunopharmacology, 10:467-473 (2010).
Clark, C.M. et al., Use of florbetapir-PET for imaging beta-amyloid pathology, JAMA, 305(3):275-83 (2011).
Correa, S.A.L. and Eales, K. L., The Role of p38 MAPK and its Substrates in Neuronal Plasticity and Neurodegenerative Disease, Journal of Signal Transduction, Hindawi Publishing Corporation, vol. 2012, Article ID 649079, 12 pp. (2012).
Extended European Search Report for EP 12782660.0, 7 pages (Nov. 6, 2014).
Garcia-Alloza, M. et al., Existing plaques and neuritic abnormalities in APP:PSI mice are not affected by administration of the gamma-secretase inhibitor LY-411575, Molecular Neurodegeneration, 4(19):1-9 (2009).
Godl et al., An efficient proteomics method to identify the cellular targets of protein kinase inhibitors, PNAS, 100(26):15434-15439 (2003).
Goldstein, D.M. et al., Selective p38alpha inhibitors clinically evaluated for the treatment of chronic inflammatory disorders, J. Med. Chem., 53(6):2345-53 (2010).
Haddad, VX-745 Vertex Pharmaceuticals, Current Opinion in Investigational Drugs, 2(8):1070-1076, (2001).
Hideshima, T. et al., Targeting p38 MAPK inhibits multiple myeloma cell growth in the bone marrow milieu, Blood, 101(2):703-5 (2003).
International Search Report for PCT/US12/37064, 4 pages (Oct. 16, 2012).
Lachman, H.J. et al., T Natural History and Outcome in Systemic AA Amyloidosis Abstract Background, New England Journal of Medicine, 2361-2371 (2007).
Lee et al., CX3CR1 Deficiency Alters Microglial Activation and Reduces Beta-Amyloid Deposition in Two Alzheimer's Disease Mouse Models, The American Journal of Pathology, 177(5):2549-2562(2010).
Lowenberg et al., Specific Inhibition of c-Raf Activity by Semapimod Induces Clinical Remission in Severe Crohn's Disease, The Journal of Immunology, 175:2293-2300 (2005).
Matousek, S. B. et al., Chronic IL-1?-mediated neuroinflammation mitigates amyloid pathology in a mouse model of Alzheimer's disease without inducing overt neurodegeneration, J. Neuroimmune Pharmacol., 7(1): 156-164 (2012).
Mayer et al., p38 MAP kinase inhibitors: A future therapy for inflammatory diseases, Drug Discovery Today: Therapeutic Strategies, 3(1):49-54 (2006).
Merlini, G. and Bellotti, V., Molecular mechanisms of amyloidosis, The New England Journal of Medicine, 349(6):583-596 (2003).
Minoshima, S. et al., Metabolic reduction in the posterior cingulate cortex in very early Alzheimer's disease, Ann. Neurol., 42(1):85-94 (1997).
Munoz, L. et al., A novel p38a MAPK inhibitor suppresses brain proinflammatory cytokine up-regulations and attenuates synaptic dysfunction and behavioral deficits in an Alzheimer's disease mouse model, Journal of Neuroinflammation, 4:21, 1-14, (2007).
Paul, M., Promising New Alzheimer's 'Drug' Halts Memory Loss, 'Drug' strikes newly identified target and could be used early in disease, Northwestern Univeristy News, 3 pages (2013) Online, last accessed Apr. 23, 2015 <http://www.northwestern.edu/newscenter/stories/2013/06/promising-new-alzheimers-drughalts-memory-loss.html>.
Reagan-Shaw et al., Dose translation from animal to human studies revisited, The FASEB Journal, 22:659-661 (2007).
Regan et al., Pyrazole Urea-Based Inhibitors of p38 MAP Kinase: From Lead Compound to Clinical Candidate, J. Med. Chem., 45:2994-3008 (2002).
Roh, et al., Stealth Attack: Plaque-Specific Antibody Allows for Efficient A? Removal without Side Effects, Neuron, 76:859-861 (2012).
Roy, S.M. et al., Targeting human central nervous system protein kinases: An isoform selective p38?MAPK inhibitor that attenuates disease progression in Alzheimer's disease mouse models, ACS Chem. Neurosci., 6(4):666-80 (2015).
Schnöder, L. et al., Deficiency of Neuronal p38α-MAPK Attenuates Amyloid Pathology in Alzheimer's Mouse and Cell Models through Facilitating Lysosomal Degradation of BACE1, J. Biol. Chem., 27 pages (2015).
Tse et al., Targeting pre-existing plaques in AD, Nature Reviews Drug Discovery, 12:100-101 (2013).
Verkaar, F. et al., Inhibition of Wnt/β-catenin signaling by p38 MAP kinase inhibitors is explained by cross-reactivity with casein kinase 1δ/ε, Chem. Biol., 18(4):485-94 (2011).
Villemagne, V.L. et al., Longitudinal assessment of Aβ and cognition in aging and Alzheimer disease, Ann. Neurol., 69(1):181-92 (2011).
Wadsworth, S.A. et al., RWJ 67657, a Potent, Orally Active Inhibitor of p38 Mitogen-Activated Protein Kinase, The Journal of Pharmacology and Experimental Therapeutics, 291(2):680-687 (1999).
Wang, D.S. et al., Memory deficits induced by inflammation are regulated by alpha5-subunit-containing GABAA receptors, Cell Rep., 2(3):488-96 (2012).
Watterson, D.M. et al., Development of Novel In Vivo Chemical Probes to Address CNS Protein Kinase Involvement in Synaptic Dysfunction, PLoS One, 8(6):e66226 (2013).
Written Opinion for PCT/US12/37064, 4 pages (Oct. 16, 2012).
Wu, Z. et al., Tonic inhibition in dentate gyrus impairs long-term potentiation and memory in an Alzheimer's disease model, Nat. Commun., 5:4159, 25 pages (2014).
Yang, S. et al., Protective Effects of p38 MAPK Inhibitor SB202190 against Hippocampal Apoptosis and Spatial Learning and Memory Deficits in a Rat Model of Vascular Dementia, BioMed Research International, Hindawi Publishing Corporation, vol. 2013, Article ID 215798, 9 pages (2013).
Yasuda, S. et al., p38 MAP kinase inhibitors as potential therapeutic drugs for neural diseases, Cent. Nerv. Syst. Agents Med. Chem., 11(1):45-59 (2011).
Zeman et al., Diagnosis of Dementia Using Nuclear Medicine Imagining Modalities, 12 Chapters on Nuclear Medicine, pp. 199-230 (2011).
Zhu et al., CD45 Deficiency Drives Amyloid-β Peptide Oligomers and Neuronal Loss in Alzheimer's Disease Mice, The Journal of Neuroscience, 31(4):1355-1365 (2011).
Zhu et al., CD45RB is a Novel Molecular Therapeutic Target to Inhibit Aβ Peptide-Induced Microglial MAPK Activation, PLoS One, 3(5):1-12 (2008).

\* cited by examiner

COMPOSITIONS AND METHODS FOR TREATING ALZHEIMER'S DISEASE

CROSS REFERENCE TO RELATED APPLICATIONS

The present application is a continuation of U.S. application Ser. No. 14/191,984, filed on Feb. 27, 2014, which is a continuation of U.S. application Ser. No. 13/467,519, filed on May 9, 2012 (issued as U.S. Pat. No. 8,697,627 on Apr. 15, 2014), which claims the benefit of U.S. Provisional Application No. 61/483,919, filed May 9, 2011, each of which are hereby incorporated by reference in their entirety.

BACKGROUND OF THE INVENTION

Alzheimer's disease is the most common cause of dementia, and is characterized by the loss of intellectual and social abilities severe enough to interfere with daily functioning. In Alzheimer's disease, healthy brain tissue degenerates, causing a steady decline in memory and mental abilities. Alzheimer's disease is not a part of normal aging, but the risk of the disorder increases with age. About 5 percent of people between the ages of 65 and 74 have Alzheimer's disease, while nearly half the people over the age of 85 have Alzheimer's.

Two types of neuron pathology, plaques and tangles, are common in patients with Alzheimer's disease. Extracellular plaques are clumps of a normally harmless protein called beta-amyloid (Aβ) which may interfere with communication between brain cells. Tangles are the internal support structure for brain cells depends on the normal functioning of a protein called tau. In people affected with Alzheimer's disease, threads of tau protein undergo alterations that cause them to become twisted. Many researchers believe this may seriously damage neurons, causing them to die and leading to memory deficit.

DETAILED DESCRIPTION OF CERTAIN EMBODIMENTS OF THE INVENTION

Definitions

Figure 1A:
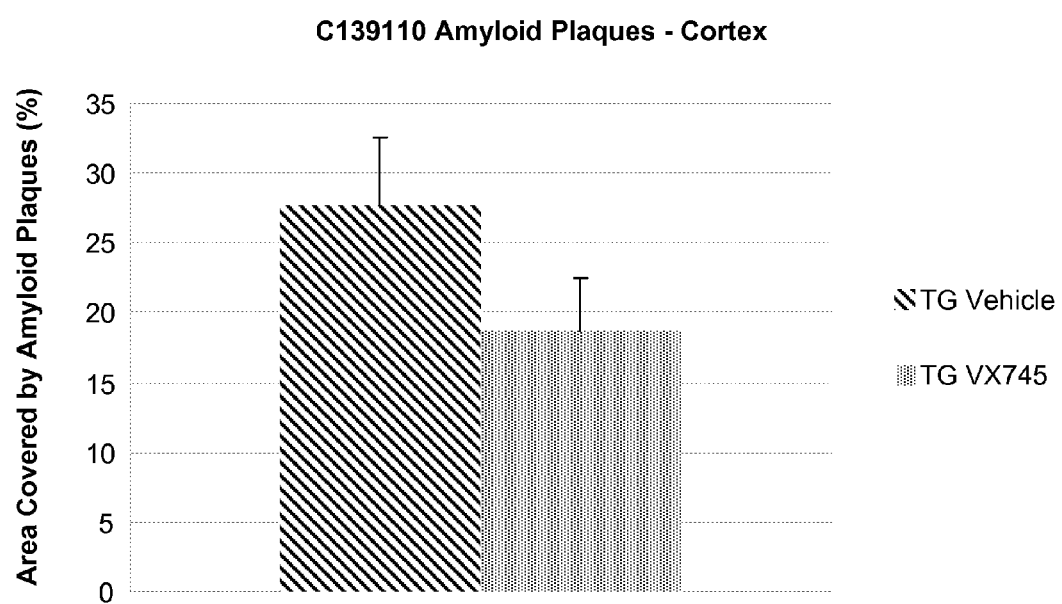
FIGS. 1A and 1B summarize the effects of VX-745 on the area percentage of amyloid plaques in the cortex (FIG. 1A) and hippocampus (FIG. 1B) following two-week administration of VX-745 (3 mg/kg BID).

Carrier: The term "carrier" refers to any chemical entity that can be incorporated into a composition containing an active agent (e.g., a p38 inhibitor) without significantly interfering with the stability and/or activity of the agent (e.g., with a biological activity of the agent). In certain embodiments, the term "carrier" refers to a pharmaceutically acceptable carrier. An exemplary carrier herein is water.

Combination. As used herein, the term "combination," "combined," and related terms refers to a subject's simultaneous exposure to two or more therapeutic agents in accordance with this invention. For example, an agent of the present invention (e.g., a p38 inhibitor) may be administered with another therapeutic agent simultaneously or sequentially in separate unit dosage forms or together in a single unit dosage form. Accordingly, the present invention provides, among other things, dosing regimens that involve administering at least an agent of the present invention (e.g., a p38 inhibitor), an additional therapeutic agent, and a pharmaceutically acceptable carrier, adjuvant, or vehicle (the pharmaceutically acceptable carrier, adjuvant, or vehicle typically being in association with one or both of the p38 inhibitor and the additional therapeutic agent).

Formulation. The term "formulation" refers to a composition that includes at least one active agent (e.g., a p38 inhibitor) together with one or more carriers, excipients or other pharmaceutical additives for administration to a patient. In general, particular carriers, excipients and/or other pharmaceutical additives are selected in accordance with knowledge in the art to achieve a desired stability, release, distribution and/or activity of active agent(s) and which are appropriate for the particular route of administration.

Low dose. The term "low dose" as used herein refers to a dose that is below the therapeutically effective amount of the reference p38 inhibitor when administered to treat a disease other than Alzheimer's disease. In some embodiments, the term "low dose" refers to a dose that is one or more orders of magnitude lower than the therapeutically effective amount of the reference p38 inhibitor when administered to treat a disease other than Alzheimer's disease. In some embodiments, the term "low dose" refers to a dose that is one-half, one-third, one-fourth, one-fifth, one-sixth, one-seventh, one-eighth or less than the therapeutically effective amount of the reference p38 inhibitor when administered to treat a disease other than Alzheimer's disease. For example, a therapeutically effective unit dose of VX-745 for the treatment of rheumatoid arthritis in humans is 250 mg. In some embodiments, a "low dose" of VX-745 is within the range of about 1 mg to about 100 mg. In some embodiments, a "low dose" of VX-745 is within the range of about 1 mg to about 50 mg. In some embodiments, a "low dose" of VX-745 is within the range of about 1 mg to about 30 mg. In some embodiments, a "low dose" of VX-745 is within the range of about 1 mg to about 10 mg. In some embodiments, a "low dose" of VX-745 is within the range of about 1 mg to about 5 mg. In some embodiments, a "low dose" of VX-745 is about 3 mg. In some embodiments, a "low dose" of VX-745 is within the range of 5-10 mg. In some embodiments, a "low dose" of VX-745 is within the range of 10-20 mg. In some embodiments, a "low dose" of VX-745 is within the range of 20-30 mg.

Neuroimaging. As used herein, the term "neuroimaging" refers to a technique which directly or indirectly images the structure or function of the brain. In some embodiments, the term "neuroimaging" refers to a technique selected from computerized axial tomography (CAT or CT), single photon emission computed tomography (SPECT), positron emission tomography (PET), magnetic resonance imaging (MRI) or functional magnetic resonance imaging (fMRI). In some embodiments, a neuroimaging technique employs one or more imaging agents such as radioactive, fluorescent or other detectable ligands. In some embodiments, a fluorescent ligand is Pittsburgh compound B ([N-Methyl-$^{11}$C]-(4'-methylaminophenyl)-6-hydroxybenzothiazole), a fluorescent analog of thioflavin T. In some embodiments, a radioactive ligand is Amyvid® (florbetapir F18) or 18F-flutemetamol. In some embodiments, the neuroimaging technique is PET scan using Pittsburgh compound B as an imaging agent. In some embodiments, the neuroimaging technique is PET scan using Amyvid® as an imaging agent. In some embodiments, the neuroimaging technique is PET scan using 18F-flutemetamol as an imaging agent.

Neuroimage. As used herein, the term "neuroimage" refers to an image or picture generated by a neuroimaging technique. In some embodiments, a "neuroimage" refers to one or more of CAT (or CT), SPECT, PET, MRI or fMRI scans.

Parenteral. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Patient. The term "patient", as used herein, means a mammal to which a formulation or composition comprising a formulation is administered, and in some embodiments includes humans.

Pharmaceutically acceptable carrier, adjuvant, or vehicle. The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Selective p38 Inhibitor. As used herein, the phrase "selective p38 inhibitor" refers to an agent which elicits a biological effect (i.e., an inhibitory or antagonistic effect) on p38 mitogen-activated protein kinase (also referred to as p38 MAPK) that is at least one order of magnitude greater than another kinase. For example, in some embodiments, a selective p38 inhibitor is an inhibitor which is selective for p38 MAPK over other protein kinases or tyrosine kinases. In some embodiments, a selective p38 inhibitor is selective for one p38 MAPK isoform over another. For example, in some embodiments, a selective p38 inhibitor refers to an inhibitor that has greater antagonistic effect against one of alpha ($\alpha$), beta ($\beta$), gamma ($\gamma$) or delta ($\delta$) p38 MAPK isoforms over another isoform. In some embodiments, a selective p38 inhibitor refers to an inhibitor that has greater antagonistic effect against the p38$\alpha$ isoform of MPAK as compared to the p38$\beta$, p38$\gamma$ and/or p38$\delta$ isoforms. Representative selective p38 inhibitors include, but are not limited to, RWJ 67657, SCIO 469, EO 1428, Org 48762-0, SD 169, SB 203580, SB 202190, SB 239063, SB 220025, VX 745, SB 242235, VX 702, SD-282, PH-797804 and others.

Therapeutic agent. As used herein, the phrase "therapeutic agent" refers to any agent that elicits a desired biological or pharmacological effect when administered to an organism.

Therapeutically effective amount and effective amount. As used herein, and unless otherwise specified, the terms "therapeutically effective amount" and "effective amount" of an agent refer to an amount sufficient to provide a therapeutic benefit in the treatment, prevention and/or management of a disease, disorder, or condition, e.g., to delay onset of or minimize (e.g., reduce the incidence and/or magnitude of) one or more symptoms associated with the disease, disorder or condition to be treated. In some embodiments, a composition may be said to contain a "therapeutically effective amount" of an agent if it contains an amount that is effective when administered as a single dose within the context of a therapeutic regimen. In some embodiments, a therapeutically effective amount is an amount that, when administered as part of a dosing regimen, is statistically likely to delay onset of or minimize (reduce the incidence and/or magnitude of) one or more symptoms or side effects of a disease, disorder or condition. In some embodiments, a "therapeutically effective amount" is an amount that enhances therapeutic efficacy of another agent with which the composition is administered in combination. In some embodiments, a therapeutically effective amount for administration to a human corresponds to a reference amount (e.g., a therapeutically effective amount in an animal model such as a mouse model) adjusted for body surface area of a human as compared with body surface area of the animal model, as is known in the art (see, for example Reagan-Shaw et al., "Dose translation from animal to human studies revisited," *The FASEB Journal* 22: 659-661 (2007), the entirety of which is herein incorporated by reference). In some embodiments, the reference therapeutically effective amount is an amount that is therapeutically effective in a mouse model, for example, as described herein. In some embodiments, the reference therapeutically effective amount is within the range of about 0.0001 mg/kg to about 500 mg/kg. In some embodiments, the reference therapeutically effective amount is within the range of about 0.0001 mg/kg to about 0.001 mg/kg. In some embodiments, the reference therapeutically effective amount is within the range of about 0.001 mg/kg to about 0.01 mg/kg. In some embodiments, the reference therapeutically effective amount is within the range of about 0.01 mg/kg to about 0.1 mg/kg. In some embodiments, the reference therapeutically effective amount is within the range of about 0.1 mg/kg to about 0.5 mg/kg. In some embodiments, the reference therapeutically effective amount is within the range of about 0.5 mg/kg to about 1 mg/kg. In some embodiments, the reference therapeutically effective amount is within the range of about 1 mg/kg to about 2.5 mg/kg. In some embodiments, the reference therapeutically effective amount is within the range of about 2.5 mg/kg to about 10 mg/kg. In some embodiments, the reference therapeutically effective amount is within the range of about 10 mg/kg to about 50 mg/kg. In some embodiments, the reference therapeutically effective amount is within the range of about 50 mg/kg to about 100 mg/kg. In some embodiments, the reference therapeutically effective amount is within the range of about 100 mg/kg to about 250 mg/kg. In some embodiments, the reference therapeutically effective amount is within the range of about 250 mg/kg to about 500 mg/kg.

Treat or Treating. The terms "treat" or "treating," as used herein, refer to partially or completely alleviating, inhibiting, delaying onset of, reducing the incidence of, yielding prophylaxis of, ameliorating and/or relieving a disorder, disease, or condition, or one or more symptoms or manifestations of the disorder, disease or condition.

Unit Dose. The expression "unit dose" as used herein refers to a physically discrete unit of a formulation appropriate for a subject to be treated (e.g., for a single dose); each unit containing a predetermined quantity of an active agent selected to produce a desired therapeutic effect when administered according to a therapeutic regimen (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. In some embodiments, a unit dose of a p38 inhibitor is about 1 mg, 3 mg, 5 mg, 10 mg, 15 mg, 20 mg, 25 mg, 30 mg, 35 mg, 40 mg, 45 mg or 50 mg.

Pathology of Alzheimer's Disease

Alzheimer's disease pathology is characterized by the deposition of extracellular amyloid plaques in the brain parenchyma and neurofibrillary tangles within neurons.

The primary component of extracellular amyloid plaques found in the brains of Alzheimer's disease patients is abnormally folded beta-amyloid protein (Aβ), a 36- to 43-amino acid peptide produced by proteolysis of amyloid precursor protein (APP) by enzymes known as secretases. APP is an integral membrane protein expressed in many tissues and concentrated in the synapses of neurons. Its primary function is not known, though it has been implicated as a regulator of synapse formation, neural plasticity and iron export. The most common isoforms of Aβ are $A\beta_{40}$ and $A\beta_{42}$; the shorter form is typically produced by cleavage that occurs in the endoplasmic reticulum, while the longer form is produced by cleavage in the trans-Golgi network. The $A\beta_{40}$ form is the more common of the two, but $A\beta_{42}$ is the more fibrillogenic and is thus associated with disease states. Mutations in APP associated with early-onset Alzheimer's have been noted to increase the relative production of $A\beta_{42}$, and thus one suggested avenue of Alzheimer's therapy involves modulating the activity of β- and γ-secretases to produce mainly $A\beta_{40}$.

In contrast, neurofibrillary tangles are intracellular aggregates of microtubule-associated protein tau (MAPT). Tau proteins, abundant in neurons in the central nervous system but less common elsewhere, stabilize microtubules. Hyperphosphorylated tau (hTau) associates with other threads of tau, eventually forming neurofibrillary tangles inside nerve cell bodies. When this occurs, the microtubules disintegrate, collapsing the neuron's transport system, resulting in malfunctions in biochemical communication between neurons and, eventually, cell death.

Recent evidence suggests that neuroinflammatory processes also contribute to the pathophysiology of Alzheimer's disease. See, e.g., Hull et al., "Pathways of Inflammatory Activation in Alzheimer's Disease: Potential Targets for Disease Modifying Drugs," *Curr. Med. Chem.* 2002, 9, 83-88, the entirety of which is incorporated herein by reference. Microglia, the resident inflammatory cells of the brain, are found in a highly activated state in the Alzheimer's disease brain, including morphological alterations, proliferation, increased expression of cell surface receptors, and secretion of inflammatory cytokines and chemokines Microglia fulfill numerous different tasks within the central nervous system (CNS) related to both immune response and the maintenance of homeostasis. The main role of microglia is phagocytosis, or the engulfing of various materials. Engulfed materials include damaged neurons, plaques, cellular debris and infectious agents such as viruses and bacteria. Microglia accumulate at the site of newly formed Aβ deposits in the Alzheimer's disease brain and may help restrict plaque growth by degrading Aβ.

Recent studies have also shown that overexpression of IL-1β, an inflammatory cytokine, leads to reduced Aβ pathology in mouse models of Alzheimer's disease. However, chronically activated microglia are also associated with inflammatory cytokines including TNFα that can substantially block the ability of the microglia to remove or degrade Aβ. Thus, the role of microglia in the pathophysiology of Alzheimer's disease is complex, with microglial activation exerting either a beneficial or detrimental effect depending on local conditions.

One signaling pathway through which neurons and microglia communicate is fractalkine (CX3CL1) and its cognate receptor (CX3CR1), a unique, one-to-one ligand-receptor chemokine pair. CX3CL1-CX3CR1 signaling has been demonstrated to play an important role in neuroinflammation and neuroprotection. Notably, CX3CL1 is highly expressed in neurons while CX3CR1 is exclusively expressed in microglia. One recent study demonstrated that the inhibition or deletion of the microglial receptor CX3CR1 leads to an amelioration of the amyloid pathology in both rapid onset and gradual onset transgenic mouse models of Alzheimer's disease. See Lee et al., "CX3CR1 Deficiency Alters Microglial Activation and Reduces Beat-Amyloid Deposition in Two Alzheimer's Disease Mouse Models," *The American Journal of Pathology*, 177(5): 2549-2562 (2010), the entirety of which is incorporated herein by reference. In fact, CX3CR1-deficient mice exhibited a dose-dependent reduction in Aβ deposition in the APPPS1 mouse model of Alzheimer's disease, suggesting that CX3CR1 deficiency harnesses the beneficial effects of microglial activation in response to Aβ. Moreover, the number of plaque-associated microglia were decreased in the knockout mice as compared to control. However, despite the reduction in the number of microglia around the Aβ deposits in the CX3CR1-deficient animals, there was observed a significant reduction in Aβ deposition, consistent with an enhanced capacity of microglia to remove Aβ. Thus, CX3CR1 signaling appears to inhibit microglial phagocytosis and prevent effective Aβ clearance. These results suggest that alterations in CX3CL1-CX3CR1 signaling can lead to altered phagocytic capabilities of microglia.

Microglial neuroinflammation also promotes MAPT phosphorylation and aggregation through the overexpression of IL-1. Recently, CX3CR1 deficiency has been shown to result in both enhanced microglial activation and MAPT phosphorylation/aggregation in humanized tau mice. Researchers observed that transgenic humanized tau mice first develop hyperphosphorylated MAPT at 3 months of age, MAPT aggregates at 9 months of age, and neuronal loss by 15 months of age. Significantly, by 12 months of age, humanized tau mice exhibited microglia in the hippocampus with shorter processes and rounder cell bodies consistent with microglial activation.

Without wishing to be bound by any particular theory, it is believed that the activation of microglia in response to such inflammatory signals, particularly neuroinflammatory processes, delays the accumulation of beta amyloid plaques associates with Alzheimer's disease. Thus, inhibition or suppression of inflammatory cascades is likely to prevent microglial activation, leading to an increase in accumulation of beta amyloid plaques and the progression of Alzheimer's disease.

p38 MAPK Inhibitors

Many extracellular stimuli, including pro-inflammatory cytokines and other inflammatory mediators, elicit specific cellular responses through the activation of mitogen-activated protein kinase (MAPK) signaling pathways. MAPKs are proline-targeted serine-threonine kinases that transduce environmental stimuli to the nucleus. Once activated, MAPKs activate other kinases or nuclear proteins through phosphorylation, including potential transcription factors and substrates. The novel mammalian reactivating protein kinase (p38/RK) MAPKs are stress-activated protein kinases that mediate responses to cellular stresses and inflammatory signals.

p38 MAPK activation occurs in the very early stages of Alzheimer's disease and is an important contributor to the inflammation of the brain. See, e.g., Bhasker et al., "Regulation of Tau Pathology by the Microglial Fractalkine Receptor," Neuron 68:19-31 (2010), the entirety of which is incorporated herein by reference. In fact, beta-amyloid fibrils in microglia stimulate rapid, transient activation of p38 MAPK resulting in inflammatory gene expression and upregulation of proinflammatory cytokines Thus, activation of the p38 MAPK pathway attenuates plaque accumulation and stimulates microglial plaque degradation.

Moreover, researchers confirmed that enhancement of MAPT phosphorylation could be blocked by preincubating neurons in vitro with a specific MAPK inhibitor, SB203580, indicating that the enhancement of MAPT phosphorylation occurred via a p38 MAPK-dependent pathway. Thus, research demonstrates that the role of p38 MAPK in Alzheimer's disease is complex, as it both stimulates microglial degradation of Aβ plaques while simultaneously promoting MAPT phosphorylation, a process which can lead to neurofibrillary tangles and loss of neuronal function. See, e.g., Munoz, et al., "Targeting p38 MAPK pathway for the treatment of Alzheimer's disease," Neuropharmacology, 58(3):561-568 (2010), incorporated herein by reference in its entirety.

The role of p38 MAPK in the various stages of inflammation has prompted the discovery of several compounds capable of inhibiting p38 (SB203580, RWJ 67657, L-167307, VX-745, RPR200765A and others). See, e.g., Kumar et al., "p38 MAP Kinases: Key Signaling Molecules as Therapeutic Targets for Inflammatory Diseases," Nature Reviews, 2:717-726 (2003); Brown et al., "p38 MAP kinase inhibitors as potential therapeutics for the treatment of joint degeneration and pain associated with osteoarthritis," J. Inflammation 5:22 (2008), the entirety of each of which is incorporated herein by reference. These pharmacological inhibitors are cytokine-suppressive anti-inflammatory drugs responsible for in vitro and in vivo inhibition of lipopolysaccharide-induced tumor necrosis factor-α (TNF-α) expression. Although p38 MAPK inhibitors have long piqued the interest of Alzheimer's disease researchers, the complexity of the disease has limited the use of such agents. More particularly, while p38 inhibitors block tau phosphorylation, the resulting decrease in the inflammatory cascades are expected to increase Aβ plaque accumulation due to the lack of microglial activation.

It has now been surprisingly found that p38 MAPK inhibitors reduce amyloid plaque burden within the central nervous system (CNS). Accordingly, the present invention encompasses the recognition that p38 MAPK inhibitors are effective for reducing amyloid plaque burden associated with Alzheimer's disease. In some embodiments, the present invention provides a method of reducing amyloid plaque burden within the central nervous system (CNS). In some embodiments, the present invention provides a method of reducing amyloid plaque burden associated with Alzheimer's disease comprising administering to a patient in need thereof a p38 MAPK inhibitor.

Exemplary p38 MAPK Inhibitors

As generally described above, there has been extensive research directed towards the discovery of p38 MAPK inhibitors for the treatment of the various stages of inflammation.

Exemplary p38 MAPK inhibitors can be found, for example, in Mayer et al., "p38 MAP kinase inhibitors: A future therapy for inflammatory diseases," Drug Discovery Today: Therapeutic Strategies 3(1): 49-54 (2006); and Regan et al., "Pyrazole Urea-Based Inhibitors of p38 MAP Kinase: from Lead Compound to Clinical Candidate," J. Med. Chem. 2002, 45, 2994-3008, the entirety of each of which are incorporated herein by reference. Table 1 lists representative p38 MAPK inhibitors.

TABLE 1

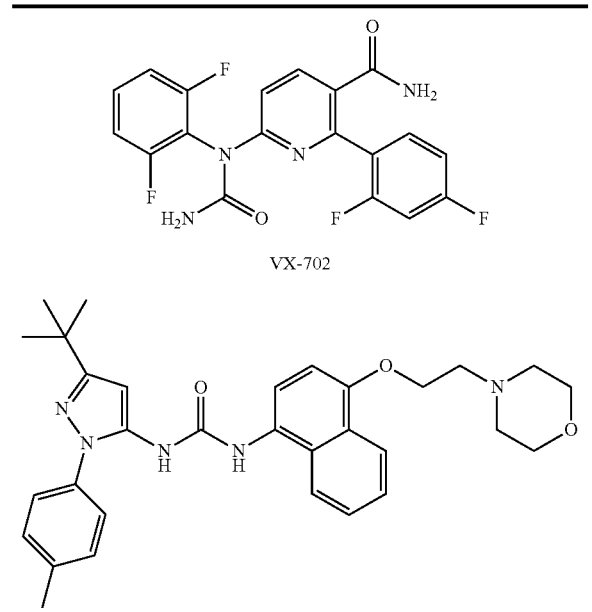

VX-702

BIRB 796 (Doramapimod)

TABLE 1-continued
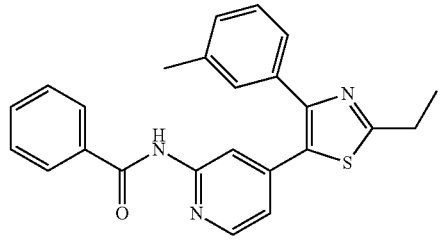 [SMILES: CCc1nc(-c2cccc(C)c2)c(-c2ccnc(NC(=O)c3ccccc3)c2)s1]
TAK-715
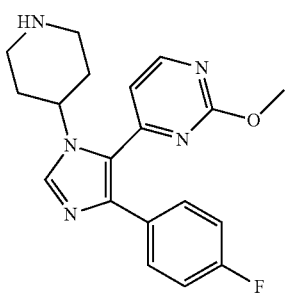
SB-242235
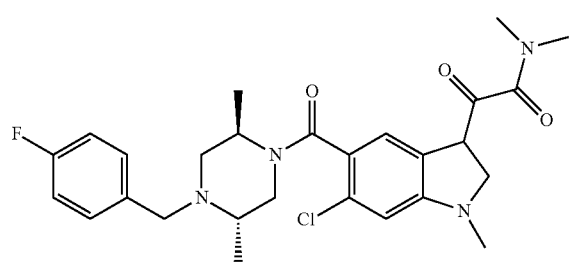 [SMILES: C[C@@H]1CN(Cc2ccc(F)cc2)[C@@H](C)CN1C(=O)c1cc2c(cc1Cl)N(C)CC2C(=O)C(=O)N(C)C]
SCIO 469
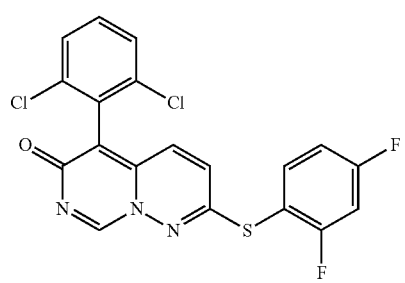
VX-745
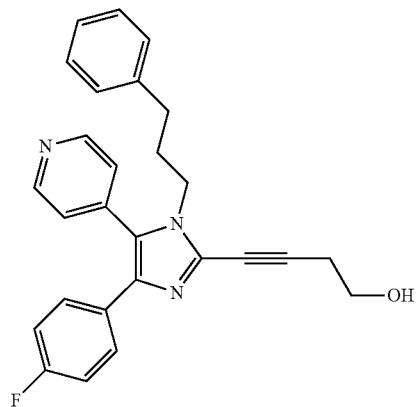 [SMILES: OCCC#Cc1nc(-c2ccc(F)cc2)c(-c2ccncc2)n1CCCc1ccccc1]
RWJ 67657
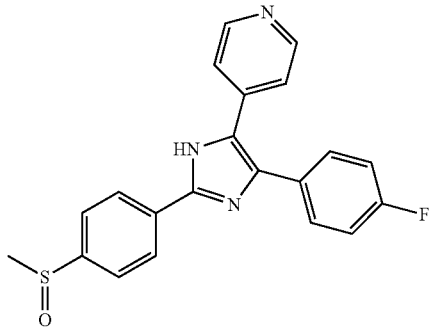
SB-203580
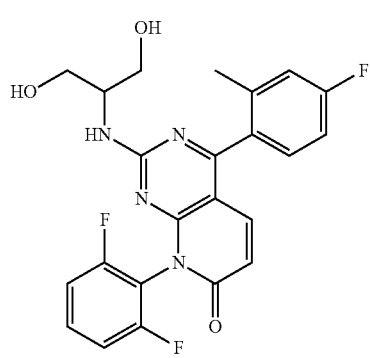 [SMILES: Cc1cc(F)ccc1-c1nc(NC(CO)CO)nc2c1ccc(=O)n2-c1c(F)cccc1F]
SB-681323
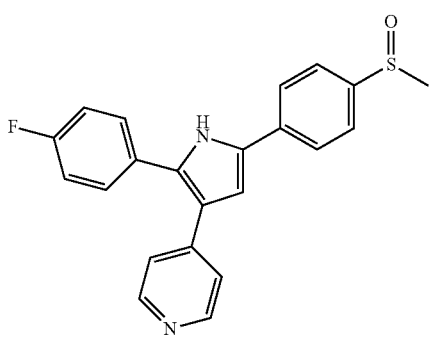 [SMILES: CS(=O)c1ccc(-c2cc(-c3ccncc3)c(-c3ccc(F)cc3)[nH]2)cc1]
L-167307

TABLE 1-continued
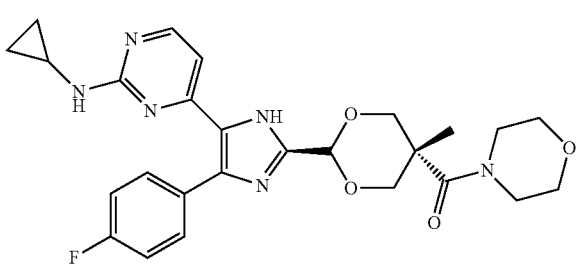
RPR-203494
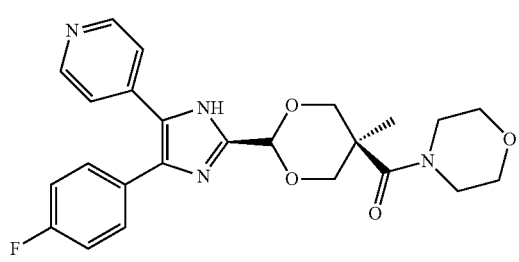
RPR-200765A
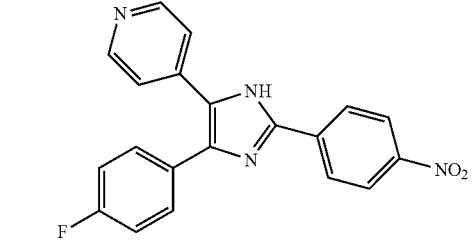 [SMILES: O=[N+]([O-])c1ccc(-c2nc(-c3ccc(F)cc3)c(-c3ccncc3)[nH]2)cc1]
PD 169316
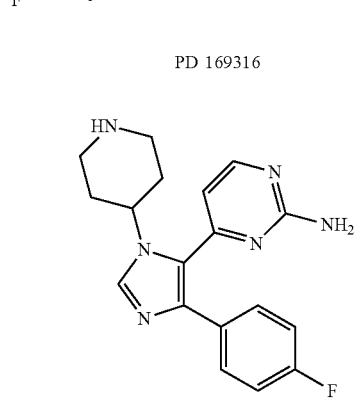
SB-200025
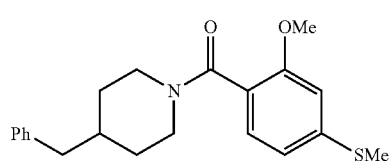 [SMILES: COc1cc(SC)ccc1C(=O)N1CCC(Cc2ccccc2)CC1]
JX 401
TABLE 1-continued
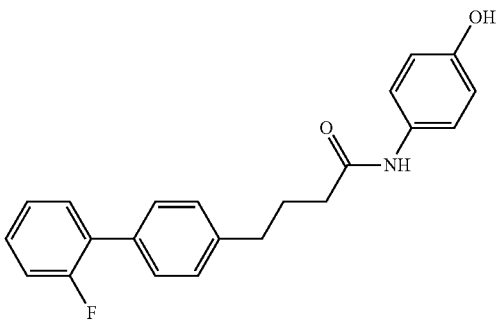 [SMILES: O=C(CCCc1ccc(-c2ccccc2F)cc1)Nc1ccc(O)cc1]
CMPD1
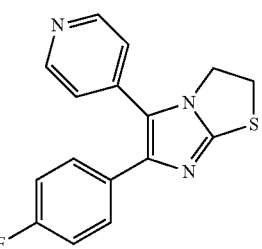
SKF 86002
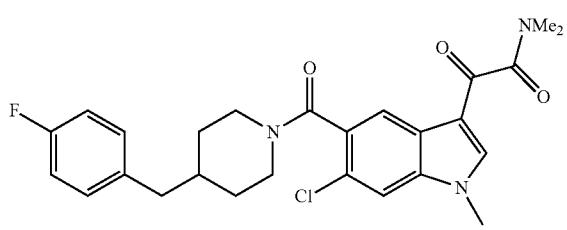 [SMILES: CN(C)C(=O)C(=O)c1cn(C)c2cc(Cl)c(C(=O)N3CCC(Cc4ccc(F)cc4)CC3)cc12]
SX 011
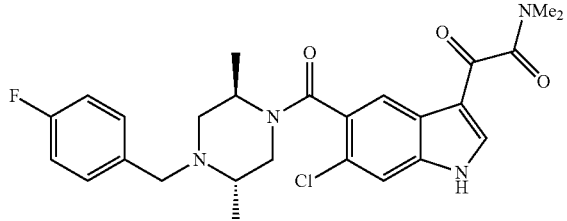
SD 282
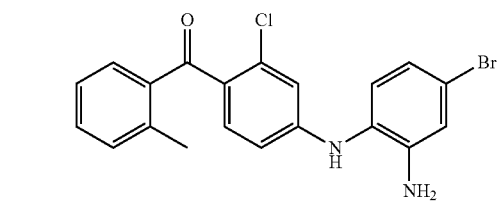 [SMILES: Cc1ccccc1C(=O)c1ccc(Nc2ccc(Br)cc2N)cc1Cl]
EO 1428
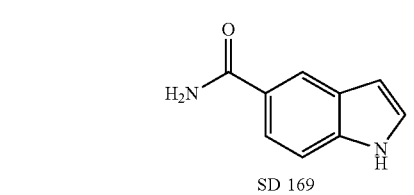
SD 169

TABLE 1-continued
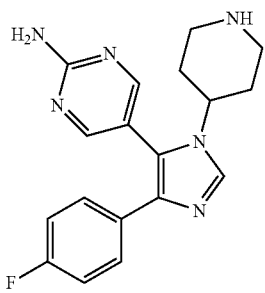 [SMILES: Nc1ncc(-c2c(-c3ccc(F)cc3)ncn2C2CCNCC2)cn1]
SB 220025
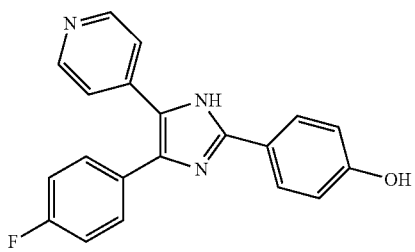 [SMILES: Oc1ccc(-c2nc(-c3ccc(F)cc3)c(-c3ccncc3)[nH]2)cc1]
SB 202190
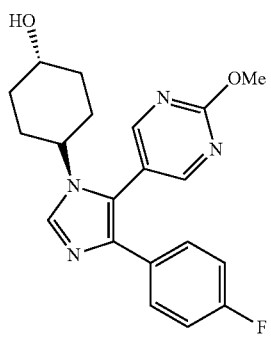
SB 239063
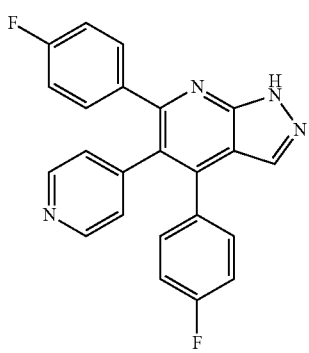 [SMILES: Fc1ccc(-c2nc3[nH]ncc3c(-c3ccc(F)cc3)c2-c2ccncc2)cc1]
Org 48762-0
TABLE 1-continued
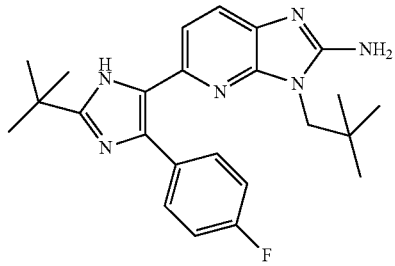 [SMILES: CC(C)(C)Cn1c(N)nc2ccc(-c3[nH]c(C(C)(C)C)nc3-c3ccc(F)cc3)nc21]
LY2228820
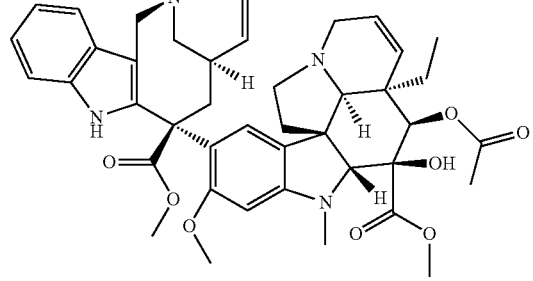
Vinorelbine
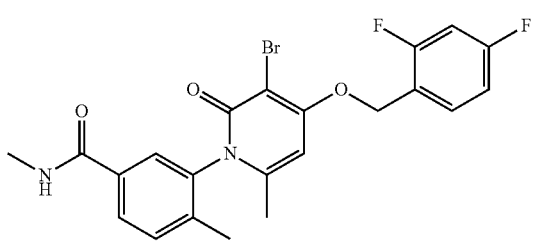 [SMILES: CNC(=O)c1ccc(C)c(-n2c(C)cc(OCc3ccc(F)cc3F)c(Br)c2=O)c1]
PH-797804
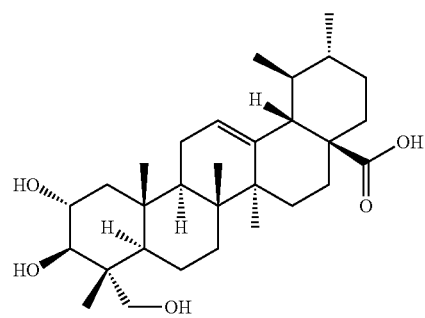
Asiatic acid TABLE 1-continued

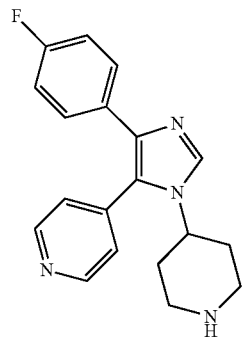 [SMILES: Fc1ccc(-c2ncn(C3CCNCC3)c2-c2ccncc2)cc1]

4-(4-(4-fluorophenyl)-1-(piperidin-4-yl)-1H-imidazol-5-yl)pyridine

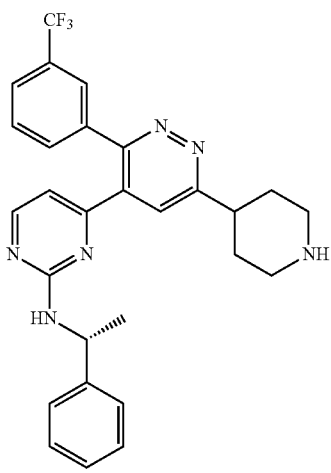 [SMILES: C[C@@H](Nc1nccc(-c2cc(C3CCNCC3)nnc2-c2cccc(C(F)(F)F)c2)n1)c1ccccc1]

(R)-N-(1-phenylethyl)-4-(6-(piperidin-4-yl)-3-(3-(trifluoromethyl)phenyl)pyridazin-4-yl)pyrimidin-2-amine

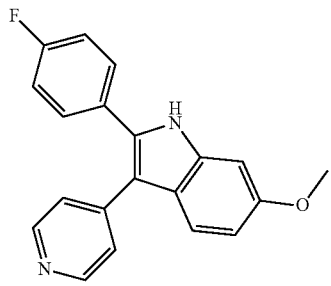 [SMILES: COc1ccc2c(-c3ccncc3)c(-c3ccc(F)cc3)[nH]c2c1]

2-(4-fluorophenyl)-6-methoxy-3-(pyridin-4-yl)-1H-indole

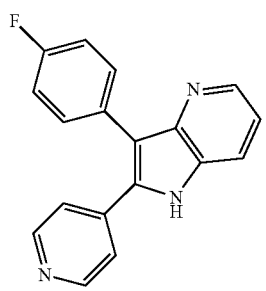 [SMILES: Fc1ccc(-c2c(-c3ccncc3)[nH]c3cccnc23)cc1]

3-(4-fluorophenyl)-2-(pyridin-4-yl)-1H-pyrrolo[3,2-b]pyridine

TABLE 1-continued

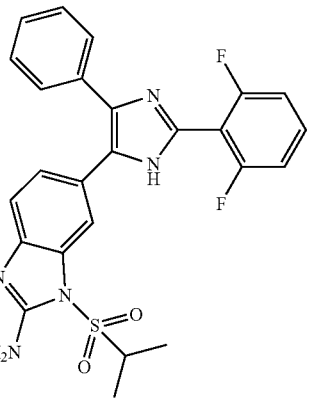

6-(2-(2,6-difluorophenyl)-4-phenyl-1H-imidazol-5-yl)-1-(isopropylsulfonyl)-1H-benzo[d]imidazol-2-amine

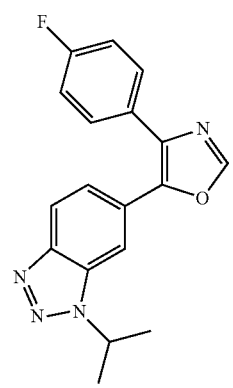 [SMILES: CC(C)n1nnc2ccc(-c3ocnc3-c3ccc(F)cc3)cc21]

4-(4-fluorophenyl)-5-(1-isopropyl-1H-benzo[d][1,2,3]triazol-6-yl)oxazole

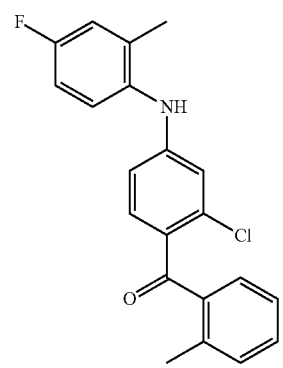 [SMILES: Cc1cc(F)ccc1Nc1ccc(C(=O)c2ccccc2C)c(Cl)c1]

(2-chloro-4-(4-fluoro-2-methylphenylamino)phenyl)(o-tolyl)methanone

TABLE 1-continued

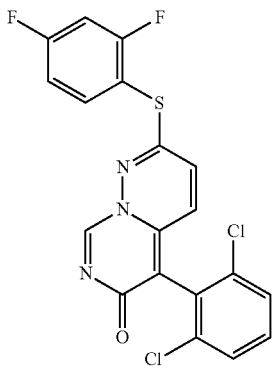 [SMILES: O=c1ncn2nc(Sc3ccc(F)cc3F)ccc2c1-c1c(Cl)cccc1Cl]

5-(2,6-dichlorophenyl)-2-(2,4-difluorophenylthio)-6H-pyrimido[1,6-b]pyridazin-6-one

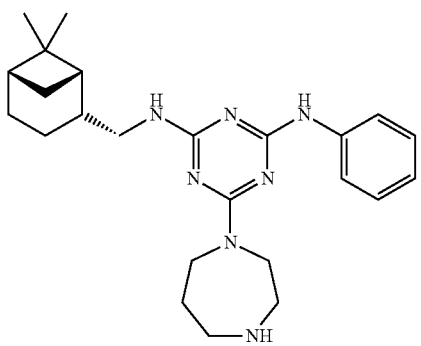

6-(1,4-diazepan-1-yl)-$N^2$-(((1S,2R,5S)-6,6-dimethylbicyclo[3.1.1]heptan-2-yl)methyl)-N4-phenyl-1,3,5-triazine-2,4-diamine

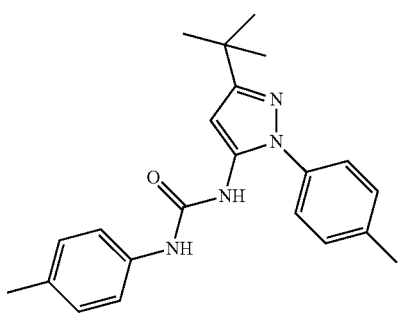

1-(3-tert-butyl-1-p-tolyl-1H-pyrazol-5-yl)-3-p-tolylurea

VX-745 is a selective small-molecule inhibitor of p38 MAPK developed by Vertex Pharmaceuticals for the treatment of rheumatoid arthritis (RA). The inhibition of MAPK by VX-745 blocks the downstream synthesis of inflammatory cytokines TNF-α, IL-1β and IL-6. Because VX-745 exhibited significant anti-inflammatory activity in rodent arthritis models, Vertex initiated a clinical trial in human rheumatoid arthritis (RA). However, patients treated with 250 mg VX-745 b.i.d. experienced adverse events, including gastrointestinal effects such as diarrhea and abdominal pain, and elevations in liver transaminases. Moreover, VX-745 is known to penetrate the blood brain barrier (BBB) in animals. In fact, animals subjected to high doses of VX-745 experienced adverse neurological effects, although these adverse events were not observed in humans. Despite validating the proof-of-concept for the inhibition of p38 MAPK as a treatment for RA, VX-745 was discontinued due to the potential for serious adverse events.

Another study utilizing VX-745 as a reference compound in an arthritis model demonstrated that a 10 mg/kg dose of VX-745 was not as effective at inhibiting paw swelling as other compounds assayed. See Chopra et al., "Pharmacological profile of AW-814141, a novel, potent, selective and orally active inhibitor of p38 MAP kinase," *International Immunopharmacology*, 10: 467-473 (2010), the entirety of which is incorporated herein by reference.

In an osteoarthritis model, VX-745 showed statistically significant inhibition of knee degeneration compared to control animals when administered to rats at 50 mg/kg. VX-745 was also assayed in a hyperalgesia model and showed significant inhibition of hyperalgesic response when administered to rats at doses of 30 mg/kg, 10 mg/kg and 3 mg/kg. The researchers discovered that the mice exhibited hyperalgesia at the 3 mg/kg, 10 mg/kg and 30 mg/kg doses. However, the researchers observed minimal effect at the 3 mg/kg dose. See Brown et al., "p38 MAP kinase inhibitors as potential therapeutics for the treatment of joint degeneration and pain associated with osteoarthritis," *J. Inflamm.*, 5:22 (2008), the entirety of which is incorporated herein by reference. Without wishing to be bound by theory, it is believed that the clinical failures of p38 inhibitors to treat chronic conditions such as rheumatoid arthritis are due to redundancy of the inflammatory pathway. Such redundancy results in the upregulation of feedback loops when p38 is chronically inhibited, leading to an overall lack of efficacy.

Methods of the Invention

As described above, in some embodiments, the present invention provides a method of reducing amyloid plaque burden within the CNS. In some embodiments, a method of reducing amyloid plaque burden comprises administering to a patient in need thereof a p38 MAPK inhibitor.

In some embodiments, a method of reducing amyloid plaque burden comprises administering to a patient in need thereof a selective p38 MAPK inhibitor.

In certain embodiments, the present invention provides a method of reducing amyloid plaque burden by administering to a patient in need thereof a low dose of a p38 MAPK inhibitor. In some embodiments, a method of reducing amyloid plaque burden comprises administering to a patient in need thereof VX-745. In some such embodiments, a method of reducing amyloid plaque burden comprises administering to a patient in need thereof a low dose of VX-745.

An agent's therapeutic efficacy is affected by the degree to which it binds blood plasma proteins. Only the fraction of unbound agent exhibits any pharmacological effect because protein-bound agents cannot traverse cell membranes or diffuse throughout the body. Thus, the more highly bound a therapeutic agent is, the lower the concentration of the agent available to elicit the desired pharmacological response. However, because there is less protein in the brain, a therapeutic agent which is capable of crossing the blood-brain barrier will have a higher concentration of free agent available to elicit the desired pharmacological response. Indeed, although it is known that VX-745 is a highly protein-bound agent, its brain levels in dogs is twice that of systemic levels.

In some embodiments, the present invention provides a method of reducing amyloid plaque burden associated with Alzheimer's disease comprising administering to a patient in need thereof a low dose of a p38 MAPK inhibitor. In some embodiments, the present invention provides a method of reducing amyloid plaque burden associated with Alzheimer's disease comprising administering to a patient in need thereof VX-745. In some embodiments, the present invention provides a method of reducing amyloid plaque burden associated with Alzheimer's disease comprising administering to a patient in need thereof a low dose of VX-745.

In some embodiments, the present invention provides a method of (i) reducing plaque burden and (ii) inhibiting MAPT phosphorylation. In some embodiments, a method of (i) reducing plaque burden and (ii) inhibiting MAPT phosphorylation comprises administering to a patient in need thereof a p38 MAPK inhibitor. In certain embodiments, a method of (i) reducing plaque burden and (ii) inhibiting MAPT phosphorylation comprises administering to a patient in need thereof a low dose of a p38 MAPK inhibitor. In some embodiments, a method of (i) reducing plaque burden and (ii) inhibiting MAPT phosphorylation comprises administering to a patient in need thereof VX-745. In certain embodiments, a method of (i) reducing plaque burden and (ii) inhibiting MAPT phosphorylation comprises administering to a patient in need thereof a low dose of VX-745.

As discussed above, while IL-1β overexpression enhances Aβ clearance, chronic activation of microglia reduces the ability of microglia to degrade Aβ. Thus, in some embodiments, the present invention provides a method of reducing plaque burden without inducing neuroinflammation. In some embodiments, a method of reducing plaque burden without inducing neuroinflammation comprises administering to a patient in need thereof a p38 MAPK inhibitor. In some embodiments, a method of reducing plaque burden without inducing neuroinflammation comprises administering to a patient in need thereof a low dose of a p38 MAPK inhibitor. In some embodiments, a method of reducing plaque burden without inducing neuroinflammation comprises administering to a patient in need thereof VX-745. In some embodiments, a method of reducing plaque burden without inducing neuroinflammation comprises administering to a patient in need thereof a low dose of VX-745.

In some embodiments, the present invention provides a method of reducing plaque burden without increasing expression and/or levels of inflammatory cytokines. In some embodiments, a method of reducing plaque burden without increasing expression and/or levels of inflammatory cytokines comprises administering to a patient in need thereof a p38 MAPK inhibitor. In some embodiments, a method of reducing plaque burden without increasing expression and/or levels of inflammatory cytokines comprises administering to a patient in need thereof a low dose of a p38 MAPK inhibitor. In some embodiments, a method of reducing plaque burden without increasing expression and/or levels of inflammatory cytokines comprises administering to a patient in need thereof VX-745. In some embodiments, a method of reducing plaque burden without increasing expression and/or levels of inflammatory cytokines comprises administering to a patient in need thereof a low dose of VX-745.

In some embodiments, the present invention provides a method of reducing plaque burden without increasing IL-1β expression and/or levels. In some embodiments, a method of reducing plaque burden without increasing IL-1β expression and/or levels comprises administering to a patient in need thereof a p38 MAPK inhibitor. In certain embodiments, the present invention provides a method of reducing plaque burden without increasing IL-1β expression and/or levels by administering to a patient in need thereof a low dose of a p38 MAPK inhibitor. In some embodiments, a method of reducing plaque burden without increasing IL-1β expression and/or levels comprises administering to a patient in need thereof VX-745. In certain embodiments, the present invention provides a method of reducing plaque burden without increasing IL-1β expression and/or levels by administering to a patient in need thereof a low dose of VX-745.

In some embodiments, the present invention provides for the administration of a p38 inhibitor, for example VX-745, once a day, twice a day, once a week, twice a week or once a month. In some embodiments, the present invention provides for the administration of a p38 inhibitor at more frequent intervals, such as one, two, three or four times per day, for up to one, two or three or more weeks, followed by a tapered dosing schedule to maintain the desired level of the p38 inhibitor. In some embodiments, the present invention provides for the administration of a p38 inhibitor at intervals of one, two, three or four times per day, for up to one, two or three or more months, followed by a tapered dosing schedule to maintain the desired level of the p38 inhibitor. More particularly, in some embodiments, the present invention provides a dosing schedule for the administration of a p38 inhibitor at intervals sufficient to achieve therapeutic levels in the brain, followed by a tapering of the dosage.

In some embodiments, the present invention provides a method of reducing the number and/or volume of amyloid plaques in a patient suffering from Alzheimer's disease comprising administering to the patient a p38 inhibitor. In some embodiments, the present invention provides a method of reducing the number and/or volume of amyloid plaques in a patient suffering from Alzheimer's disease comprising administering to the patient a low dose of a p38 inhibitor. In some embodiments, the present invention provides a method of reducing the number and/or volume of amyloid plaques in a patient suffering from Alzheimer's disease comprising administering to the patient a therapeutically effective dose of VX-745. In some embodiments, the present invention provides a method of reducing the number and/or volume of amyloid plaques in a patient suffering from Alzheimer's disease comprising administering to the patient a low dose of VX-745.

In some embodiments, the present invention provides a method of reducing the number and/or volume of amyloid plaque $A\beta_{42}$ in a patient suffering from Alzheimer's disease comprising administering to the patient a p38 inhibitor. In some embodiments, the present invention provides a method of reducing the number and/or volume of amyloid plaque $A\beta_{42}$ in a patient suffering from Alzheimer's disease comprising administering to the patient a low dose of a p38 inhibitor. In some embodiments, the present invention provides a method of reducing the number and/or volume of amyloid plaque $A\beta_{42}$ in a patient suffering from Alzheimer's disease comprising administering to the patient VX-745. In some embodiments, the present invention provides a method of reducing the number and/or volume of amyloid plaque $A\beta_{42}$ in a patient suffering from Alzheimer's disease comprising administering to the patient a low dose of VX-745.

In some embodiments, the present invention provides a method of reducing the number and/or volume of a beta amyloid plaque in a patient suffering from Alzheimer's disease comprising administering to the patient a therapeutically effective dose of a p38 inhibitor. In some embodiments, the present invention provides a method of reducing the number and/or volume of a beta amyloid plaque in a patient suffering from Alzheimer's disease comprising administering to the patient a therapeutically effective dose of VX-745. In some embodiments, the present invention provides a method of reducing the number and/or volume of amyloid plaque Aβ$_{42}$ in a patient suffering from Alzheimer's disease comprising administering to the patient a low dose of a p38 inhibitor. In some embodiments, the present invention provides a method of reducing the number and/or volume of amyloid plaque Aβ$_{42}$ in a patient suffering from Alzheimer's disease comprising administering to the patient a low dose of VX-745.

In some embodiments, the present invention provides a method for preventing the accumulation of amyloid plaques comprising the administration to a patient in need thereof a therapeutically effective amount of a p38 inhibitor. In some embodiments, the present invention provides a method for preventing the accumulation of amyloid plaques comprising the administration to a patient in need thereof a therapeutically effective amount of a low dose of a p38 inhibitor. In some embodiments, the present invention provides a method for preventing the accumulation of amyloid plaques comprising the administration to a patient in need thereof a therapeutically effective amount of VX-745. In some embodiments, the present invention provides a method for preventing the accumulation of amyloid plaques comprising the administration to a patient in need thereof a therapeutically effective amount of a low dose of VX-745.

In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 1 mg to about 50 mg. In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 1 mg to about 20 mg. In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 1 mg to about 10 mg. In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 1 mg to about 5 mg. In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 5 mg to about 10 mg. In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 10 mg to about 20 mg. In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 20 mg to about 30 mg. In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 30 mg to about 40 mg. In some embodiments, the present invention provides a method of reducing the number and/or volume of amyloid plaques in a patient suffering from Alzheimer's disease comprising administering to the patient a therapeutically effective dose of a p38 inhibitor, wherein the therapeutically effective dose is between about 40 mg to about 50 mg.

In some embodiments, the present invention provides an amyloid plaque clearance mechanism comprising administering to a subject in need thereof a p38 MAPK inhibitor.

In some embodiments, the present invention provides a method of reducing plaque burden in a patient in need thereof, said method comprising administering to said patient a p38 MAPK inhibitor for a period of less than about 6 months. In some embodiments, the present invention provides a method of reducing plaque burden in a patient in need thereof, said method comprising administering to said patient a p38 MAPK inhibitor for a period of less than about 4 months. In some embodiments, the present invention provides a method of reducing plaque burden in a patient in need thereof, said method comprising administering to said patient a p38 MAPK inhibitor for a period of less than about 2 months. In some embodiments, the present invention provides a method of reducing plaque burden in a patient in need thereof, said method comprising administering to said patient a p38 MAPK inhibitor for a period of less than about 1 month. In some embodiments, the present invention provides a method of reducing plaque burden in a patient in need thereof, said method comprising administering to said patient a p38 MAPK inhibitor for a period of less than about 2 weeks.

In some embodiments, the present invention provides a method of reducing amyloid plaque burden, said method comprising:
 (i) imaging the brain of a subject to produce a neuroimage;
 (ii) comparing the neuroimage to a reference image to determine the number and/or area of the amyloid plaques; and
 (iii) administering a therapeutically effective amount of a p38 inhibitor if the subject is determined to have an increased amount of amyloid plaques when compared to the reference image.

In some embodiments, the present invention provides a method of reducing amyloid plaque burden, said method comprising:
 (i) imaging the brain of a subject;
 (ii) determining the number and/or area of the amyloid plaques; and
 (iii) administering a therapeutically effective amount of a p38 inhibitor if the number and/or area of the amyloid plaques exceeds a predetermined threshold.

In some embodiments, the reference image is an image of a control subject. In some embodiments, the reference image is an image of a subject having normal cognitive function. In some embodiments, the reference image is a baseline image of the subject's brain. In some such embodiments, the reference image is a prior scan of the subject's brain. In some embodiments, the subject is at risk for developing Alzheimer's disease.

In some embodiments, steps of (i) imaging, (ii) comparing amyloid plaques to a reference image and/or determining the number and/or area of amyloid plaques and (iii) administering a p38 inhibitor are repeated at one or more predetermined intervals. In some such embodiments, a predetermined interval is one month, two months, three months, four months, five months, six months, seven months, eight months, nine months, ten months, eleven months, twelve months. In some embodiments, a predetermined interval is one year, two years, three years, four years or five years. In some embodiments, the predetermined interval is six (6) months.

In some embodiments, the subject is a patient at risk of developing or suffering from Alzheimer's disease.

In some embodiments, the brain of a subject is imaged using one or more neuroimaging techniques. In some embodiments, the neuroimaging technique is selected from the group consisting of computerized axial tomography (CAT or CT), single photon emission computed tomography (SPECT), positron emission tomography (PET), magnetic resonance imaging (MRI) or functional magnetic resonance imaging (fMRI). In some embodiments, the neuroimaging technique is computerized axial tomography (CAT or CT). In some embodiments, the neuroimaging technique is positron emission tomography (PET). In some such embodiments, the imaging agent used in the PET scan is selected from AMYVID or Pittsburgh compound B. In some embodiments, the neuroimaging technique is magnetic resonance imaging (MM). In some embodiments, the neuroimaging technique is functional magnetic resonance imaging (fMRI).

A person of ordinary skill understands how to determine or measure the number and/or area of the amyloid plaques in a neuroimage. For example, see Zeman et al., "Diagnosis of Dementia Using Nuclear Medicine Imaging Modalities," Chapter 8, 12 *Chapters on Nuclear Medicine*, Gholamrezanezhad, Ed., 199-229 (Dec. 22, 2011) and Hsiao et al., "Correlation of early-phase $^{18}$F-florbetapir (AV-45/AMYVID) PET images to FDG images: preliminary studies," *European Journal of Nuclear Medicine and Molecular Imaging*, 39(4), 613-620 (2012), the entirety of each of which is hereby incorporated by reference in its entirety.

In some embodiments, a p38 inhibitor is administered for a period of less than six (6) months. In some embodiments, a p38 inhibitor is administered for a period of less than four (4) months. In some embodiments, a p38 inhibitor is administered for a period of less than two (2) months. In some embodiments, a p38 inhibitor is administered for a period of less than one (1) month. In some embodiments, a p38 inhibitor is administered for a period of less than three (3) weeks. In some embodiments, a p38 inhibitor is administered for a period of less than two (2) weeks. In some embodiments, a p38 inhibitor is administered for a period of less than one (1) week.

In some embodiments, a predetermined threshold is a baseline for a particular subject. For example, in some embodiments, the brain of a subject at risk for developing Alzheimer's disease is imaged and the number and/or area of amyloid plaques is determined and/or measured. The number and/or area of the plaques is that subject's baseline or predetermined threshold against which all later brain images are compared.

In some embodiments, a predetermined threshold is based on the number and/or area of amyloid plaques typically found in an Alzheimer's diseased brain. In some such embodiments, a predetermined threshold is an average of the number and/or area of amyloid plaques typically found in an Alzheimer's diseased brain.

In some embodiments, the present invention provides a method of reducing amyloid plaque burden in a subject suffering from or at risk for developing Alzheimer's disease, said method comprising:

(iv) imaging the brain of a subject;
(v) determining the number and/or area of the amyloid plaques; and
(vi) administering a therapeutically effective amount of a p38 inhibitor if the number and/or area of the amyloid plaques exceeds a predetermined threshold.

In some embodiments, the present invention provides a method of treating a subject suffering from amyloid plaques, wherein the number and/or area of the amyloid plaques exceeds a predetermined threshold, said method comprising administering to the subject a therapeutically effective amount of a p38 inhibitor.

In some embodiments, the present invention provides a method of treating a subject suffering from amyloid plaques, wherein the number and/or area of the amyloid plaques exceeds a predetermined threshold, said method comprising:

(i) administering a therapeutically effective amount of a p38 inhibitor for a period of less than six (6) months;
(ii) imaging the brain of the subject at regular intervals; and
(iii) administering a therapeutically effective amount of a p38 inhibitor if the number and/or area of the amyloid plaques exceeds the previously measured amyloid plaque level.

In some such embodiments, the subject is administered a p38 inhibitor for a period of less than four (4) months, less than two (2) months, less than one (1) month, or less than two (2) weeks.

In some embodiments, the present invention provides a method of treating a subject suffering from amyloid plaques, wherein the number and/or area of the amyloid plaques exceeds a predetermined threshold as measured by one or more neuroimaging techniques, said method comprising administering a therapeutically effective amount of a p38 inhibitor for a period of less than six (6) months. In some such embodiments, the neuroimaging technique is a PET scan. In some embodiments, the method further comprises (i) imaging the brain of the subject at regular intervals; and (ii) administering a therapeutically effective amount of a p38 inhibitor if the number and/or area of the amyloid plaques exceeds the previously measured amyloid plaque level.

Combination Therapies

In certain embodiments, the present invention provides a method of treating Alzheimer's disease comprising administering to a subject a therapeutically effective amount of a p38 inhibitor together with one or more additional therapeutic agents. In some embodiments, the present invention provides a method of treating Alzheimer's disease comprising administering to a subject a therapeutically effective amount of a p38 inhibitor together with one or more additional therapeutic agents selected from cholinesterase inhibitors, N-methyl-D-aspartate antagonists, vitamin E, antidepressants, anxiolytics, antipsychotics, mood stabilizers and sleep aids.

Representative cholinesterase inhibitors include, without limitation, donepezil (Aricept®), rivastigmine (Exelon®), galantamine (Razadyne®) and tacrine (Cognex®).

Representative antidepressants include, without limitation, bupropion (Wellbutrin®), citalopram (Celexa®), fluoxetine (Prozac®), mirtazapine (Remeron®), paroxetine (Paxil®), sertraline (Zoloft®), trazodone (Desyrel®), venlafaxine (Effexor®), nortriptyline (Pamelor®) and desipramine (Norpramine®).

Representative anxiolytics include, without limitation, lorazepam (Ativan®) and oxazepam (Serax®).

Representative antipsychotics include, without limitation, aripiprazole (Abilify®), clozapine (Clozaril®), haloperidol (Haldol®), olanzapine (Zyprexa®), quetiapine (Seroquel®), risperidone (Risperdal®) and ziprasidone (Geodon®).

Representative mood stabilizers include, without limitation, carbamazepine (Tegretol®) and divalproex (Depakota®).

Representative sleep aids include, without limitation, zolpidem, zaleplon and chloral hydrate.

Representative N-methyl-D-aspartate antagonists include, without limitation, memantine (Namenda®).

In some embodiments, the present invention provides a method of treating Alzheimer's disease comprising administering to a subject a therapeutically effective amount of a p38 inhibitor together with one or more additional therapeutic agents selected from the group consisting of exenatide (Byetta®), varenicline, PF-04360365, rivastigmine, LY450139, ST101, bryostatin, EVP-6124, atomoxetine, HF0220, resveratrol, galantamine, PF-01913539, semagacestat, 3APS, immunoglobulin, dimebon, alpha-tocopherol, BAY85-8101, estrogen, progesterone, ACC-001, ginko biloba, nicergoline, piracetam, NIC5-15, xaliproden (SR57746A), indomethacin, DMXB-A, LY2062430, 11-C PIB, bapineuzumab, etanercept, ramipril, interferon beta-1a, simvastatin, lipoic acid, fish oil, curcumin, PF-04447943, folate, vitamin B6, vitamin B12, leuprolide, INM-176, AH110690, tryptophan, SK-PC-B70M, BMS-708163, escitalopram, TRx0014, BAY94-9172, cerebrolysin, epigallocatechin-galate, SB-742457, lithium, rosiglitazone, divalproex, SAR110894D, PRX-03140, CX516 (Ampalex), nicotinamide, rasagiline, AC-1202 (Ketasyn®), enduramide, neramexane, razadyne, NS 2330 (Tesofensine®), tamibarotene, acitretin, methylphenidate, mifepristone, ZT-1, AFFITOPE AD01, AFFITOPE AD02, GSK239512, GSK933776, SR57667B, PPI-1019, MPC-7869, AZD3480, PAZ-417, solanezumab, masitinib (AB1010), BAY1006578, docosahexaenoic acid, QS-21, MNI-558, reminyl retard, flutemetamol, estradiol, medroxyprogesterone, valproate, T-817MA, AZD1446, AAB-003 (PF-05236812), modafinil, raloxifene, atorvastatin, doxycycline, trazadone, sodium oxybate, huperzine A, lutein, zeaxanthin, AC-3933, dextroamphetamine, EPAX 1050TG, SRA-333, MNI-168, CAD106, SGS742, NP031112, SSR180711C, GSI-953, prazosin, MEM 1003, AndroGel, AVE1625, cyclophosphamate, TC-5619-238, MK0249, lecozotan, circadin, MEM 3454, PPI-1019, UB 311, PF-04494700, ABT-089, LY451395, E2020, Rofecoxib, PF-03654746, EHT 0202 etazolate, DCB-AD1, ONO-2506P0, EGb761®, gantenerumab, florbetapir, ELND005, prednisone, novasoy, ginseng, pioglitazone, caprylidene, ABT-288, ABT-384, nefiracetam, AQW051, Pitavastatin, naproxen sodium (Aleve®), lornoxicam, AN-1792, SR57667B, melatonin, SAM-531, MK0952, MK0677, IFN-alpha2A, BAY 94-9172, PYM50028, lecozotan SR, thalidomide, tramiprosate, FK962, IVIG, R05313534, bifeprunox, LNK-754, ELND005, NSA-789, ramelteon, Florbetaben, SRA-444, VP4896, celecoxib, hydrocodone, GSI-136, Zolpidem, MK3328, metformin, CTS21166, elontril, ibuprofen, posiphen tartrate, JNJ-39393406, testosterone, BRL-049653, BMS-708163, SAM-315, ketoconazole, fluconazole, warfarin, E2609, AZD0328, LY2886721, CHF 5074, E2212, acetaminophen, LY2811376, ABT-126, melatonin, GSK1034702, armodafinil, depakote, gemfibrozil, AL-108, levetiracetam, and quinacrine.

Pharmaceutical Compositions

In some embodiments, the present invention provides a pharmaceutical composition comprising a p38 MAPK inhibitor together with one or more therapeutic agents and a pharmaceutically acceptable carrier, adjuvant, or vehicle. In some embodiments, the present invention provides a pharmaceutical composition comprising a low dose of a p38 MAPK inhibitor together with one or more therapeutic agents and a pharmaceutically acceptable carrier, adjuvant, or vehicle. In some embodiments, the present invention provides a pharmaceutical composition for treating Alzheimer's disease comprising a p38 inhibitor and one or more pharmaceutically acceptable excipients. In some embodiments, the present invention provides a pharmaceutical composition for treating Alzheimer's disease comprising a p38 inhibitor selected from VX-702, VX-745, BIRB 796, TAK-715, SCIO 469, RWJ 67657, SB 681323, SB 242235, SB 203580, L-167307, RPR-203494, RPR-200765A, PD 169316, SB 200025, JX 401, CMPD1, SKF 86002, SX 011, SD 282, EO 1428, SD 169, SB 220025, SB 202190, SB 239063, Org 48762-0, LY2228820, vinorelbine, PH-797804 and asiatic acid, and one or more pharmaceutically acceptable excipients. In some such embodiments, a pharmaceutical composition for treating Alzheimer's disease comprises a low dose p38 inhibitor. In some embodiments, the present invention provides a pharmaceutical composition for treating Alzheimer's disease comprising VX-745. In some such embodiments, a pharmaceutical composition comprises a low dose of VX-745.

In some embodiments, the present invention provides a pharmaceutical composition comprising VX-745 together with one or more therapeutic agents and a pharmaceutically acceptable carrier, adjuvant, or vehicle. In some embodiments, the present invention provides a pharmaceutical composition comprising a low dose of VX-745, one or more therapeutic agents and a pharmaceutically acceptable carrier, adjuvant, or vehicle. In some embodiments, the present invention provides a pharmaceutical composition comprising a low dose of VX-745, one or more therapeutic agents selected from donepezil (Aricept®), rivastigmine (Exelon®), galantamine (Razadyne®), tacrine (Cognex®), bupropion (Wellbutrin®), citalopram (Celexa®), fluoxetine (Prozac®), mirtazapine (Remeron®), paroxetine (Paxil®), sertraline (Zoloft®), trazodone (Desyrel®), venlafaxine (Effexor®), nortriptyline (Pamelor®), desipramine (Norpramine®), lorazepam (Ativan®), oxazepam (Serax®), aripiprazole (Abilify®), clozapine (Clozaril®), haloperidol (Haldol®), olanzapine (Zyprexa®), quetiapine (Seroquel®), risperidone (Risperdal®), ziprasidone (Geodon®), carbamazepine (Tegretol®), divalproex (Depakota®), zolpidem, zaleplon, chloral hydrate, memantine (Namenda®), exenatide (Byetta®), varenicline, PF-04360365, rivastigmine, LY450139, ST101, bryostatin, EVP-6124, atomoxetine, HF0220, resveratrol, galantamine, PF-01913539, semagacestat, 3APS, immunoglobulin, dimebon, alpha-tocopherol, BAY85-8101, estrogen, progesterone, ACC-001, ginko biloba, nicergoline, piracetam, NIC5-15, xaliproden (SR57746A), indomethacin, DMXB-A, LY2062430, 11-C PIB, bapineuzumab, etanercept, ramipril, interferon beta-1a, simvastatin, lipoic acid, fish oil, curcumin, PF-04447943, folate, vitamin B6, vitamin B12, leuprolide, INM-176, AH110690, tryptophan, SK-PC-B70M, BMS-708163, escitalopram, TRx0014, BAY94-9172, cerebrolysin, epigallocatechin-galate, SB-742457, lithium, rosiglitazone, divalproex, SAR110894D, PRX-03140, CX516 (Ampalex), nicotinamide, rasagiline, AC-1202 (Ketasyn®), enduramide, neramexane, razadyne, NS 2330 (Tesofensine®), tamibarotene, acitretin, methylphenidate, mifepristone, ZT-1, AFFITOPE AD01, AFFITOPE AD02, GSK239512, GSK933776, SR57667B, PPI-1019, MPC-7869, AZD3480, PAZ-417, solanezumab, masitinib (AB1010), BAY1006578, docosahexaenoic acid, QS-21, MNI-558, reminyl retard, flutemetamol, estradiol, medroxyprogesterone, valproate, T-817MA, AZD1446, AAB-003 (PF-05236812), modafinil, raloxifene, atorvastatin, doxycycline, trazadone, sodium oxybate, huperzine A, lutein, zeaxanthin, AC-3933, dextroamphetamine, EPAX 1050TG, SRA-333, MNI-168, CAD106, SGS742, NP031112, SSR180711C, GSI-953, prazosin, MEM 1003, AndroGel, AVE1625, cyclophosphamate, TC-5619-238, MK0249, lecozotan, circadin, MEM 3454, PPI-1019, UB 311, PF-04494700, ABT-089, LY451395, E2020, Rofecoxib, PF-03654746, EHT 0202 etazolate, DCB-AD1, ONO-2506PO, EGb761®, gantenerumab, florbetapir, ELND005, prednisone, novasoy, *ginseng*, pioglitazone, caprylidene, ABT-288, ABT-384, nefiracetam, AQW051, Pitavastatin, naproxen sodium (Aleve®), lornoxicam, AN-1792, SR57667B, melatonin, SAM-531, MK0952, MK0677, IFN-alpha2A, BAY 94-9172, PYM50028, lecozotan SR, thalidomide, tramiprosate, FK962, IVIG, R05313534, bifeprunox, LNK-754, ELND005, NSA-789, ramelteon, Florbetaben, SRA-444, VP4896, celecoxib, hydrocodone, GSI-136, Zolpidem, MK3328, metformin, CTS21166, elontril, ibuprofen, posiphen tartrate, JNJ-39393406, testosterone, BRL-049653, BMS-708163, SAM-315, ketoconazole, fluconazole, warfarin, E2609, AZD0328, LY2886721, CHF 5074, E2212, acetaminophen, LY2811376, ABT-126, melatonin, GSK1034702, armodafinil, depakote, gemfibrozil, AL-108, levetiracetam, and quinacrine, and a pharmaceutically acceptable carrier, adjuvant, or vehicle.

In certain embodiments, pharmaceutically acceptable compositions of this invention are formulated for oral administration. Pharmaceutically acceptable compositions of this invention may be orally administered in any orally acceptable dosage form including, but not limited to, capsules, caplets, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

The quantities of the compounds of the present invention that are combined with the carrier materials to produce a composition in a single dosage form will vary depending upon the patient and the particular mode of administration. Preferably, provided compositions should be formulated so that a dosage of between 1-50 mg/day of the p38 inhibitor (ie, VX-745 or other p38 inhibitor) can be administered to a patient receiving these compositions. Examples of compositions include compositions formulated to administer dosages of between 1-10 mg, 10-25 mg or 25-50 mg per day of the p38 inhibitor to the patient receiving these compositions. In other embodiments of the invention, compositions include compositions formulated to administer dosages of between 3-5 mg, 5-10 mg, 10-20 mg, 20-30 mg, 30-40 mg or 40-50 mg, per day of the inhibitor to the patient receiving these compositions. In some embodiments, the composition is formulated into doses containing 1 mg, 3 mg, 5 mg, 10 mg, 20 mg, 25 mg, 30 mg or 50 mg of the active composition. Dosing regimens for these formulations may include but are not limited to single administration dosing, once, twice, or three times daily dosing, weekly dosing, and monthly dosing.

In some treatment regimens, patients will be initially treated with larger doses of the compounds of the present invention ("loading dose") for a certain period of time ("loading period") in order to achieve a high tissue concentration of the drug, before being treated with lower doses of active composition ("maintenance dose") for a longer period of time ("maintenance period") in order to maintain the serum or tissue concentration of the active composition.

In some treatment regimens, administration of the inhibitor to a patient is temporarily halted (a "drug holiday"). In some examples, a patient may have cycles of daily doses of inhibitor for a month followed by a one month holiday. In another example, a patient might have daily dosing of an inhibitor for six months, followed by a one month holiday. In another example, a patient might have daily doses of an inhibitor for three weeks followed by a one week holiday. In yet another example, a patient might have daily doses of a drug for one week, followed by a three week holiday. In another example, a patient might have cycles of weekly doses of a drug for 6 weeks, followed by a three week holiday.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

EXEMPLIFICATION

Example 1

The purpose of the study was to evaluate the effect of 2 week twice a day oral VX-745 treatment on beta amyloid (Aβ) accumulation and plaque load and inflammation in Alzheimer's disease (AD) transgenic Tg2576 mouse model.

Animals.

Transgenic mice were treated either with vehicle or VX-745 for 2 weeks starting at 26 months of age. After 2 weeks of treatment the animals were terminated, and the brains were used for biochemical and immunohistological analyses for insoluble amyloid beta levels and plaque load by Aβ1-42 ELISA and Aβ immunohistochemistry. Inflammation was analyzed by ventral cortex IL-1β and TNF-α ELISA and microgliosis by CD11b immunohistochemistry. Plasma was collected at end-point and sent to client for PK analysis.

All animal experiments were carried out according to the National Institute of Health (NIH) guidelines for the care and use of laboratory animals, and approved by the State Provincial Office of Southern Finland. Female transgenic Tg2576 mice (n=12) and wild-type mice (n=5), purchased from Taconic, were used for the experiment. Animals were housed at a standard temperature (22±1° C.) and in a light-controlled environment (lights on from 7 am to 8 pm) with ad libitum access to food and water. The Tg2576 transgenic line was developed through insertion of the hAPP695 construct with the 'Swedish' double mutation and hamster prion protein cosmid vector into a C57B6/JxSJL host; the prion promoter limits overexpression of mutant APP to neurons in the brain. Consequently, the Tg2576 mouse develops elevated brain levels of soluble Aβ1-40 and Aβ1-42 by 6-8 months of age and Aβ-containing neuritic plaques in the neocortex and hippocampus by 10-16 months. The mice were divided into treatment groups as follows:

5 wild-type control mice treated with Vehicle
6 Tg2576 mice treated with Vehicle
6 Tg2576 mice treated with VX-745 (3 mg/kg)
Compound Storage and Instructions for Formulation.

VX-745 was delivered to Cerebricon as dry compound by the sponsor. The vehicle to be utilized was 1% Pluronic F108. The storage and dissolving instructions were provided by the sponsor. Material safety data sheet or similar document of the compound was provided by the sponsor. The solutions were stored according to instructions provided by the sponsor (storage conditions and expiration day of solution). Vehicle was provided by the sponsor/Cerebricon.

Drug Delivery.

The oral administration of VX-745 or vehicle by oral gavage (10 ml/kg) was done BID starting at the age of 26 months and continuing for 14 days. On the day of termination, treatment was given 2 hours prior to termination.

General Health Status and Humane End-Points.

Animals were monitored twice-a-day by laboratory personnel (8 am and 4 pm). In cases where general health status of an animal significantly worsened, the mouse was terminated by an overdose of $CO_2$, decapitated and brains processed as detailed below. Definitions of acceptable end-points included: no spontaneous movements and inability to drink or eat in 24-h observation period, massive bleeding, spontaneous inflammation, missing anatomy, swelling or tumors.

Collection of Plasma and Brain Samples.

Two hours after the last dosing the mice were deeply anesthetized with sodium pentobarbital (60 mg/kg Mebunat, Orion Pharma, Finland). The mice were subjected to cardiac puncture and blood samples were collected into pre-cooled (ice bath) EDTA tubes. The tubes were kept on ice and plasma was separated by centrifugation at 2000 g (+4° C.) as soon as possible. 150-200 µl of plasma from each mouse was transferred into pre-cooled polypropylene tubes and kept frozen at −80° C. until sent to the sponsor for PK analysis.

The brains were perfused with non-heparinized saline. Right hemisphere was post-fixed by immersion in 4% PFA in 0.1 M PB. After a brief wash with phosphate buffer, it was cryoprotected in 30% sucrose in PB for 2-3 days, after which it was frozen on liquid nitrogen and stored at −80° C. for further analysis (immunohistochemistry). Left hemisphere (dissected on ice to hippocampus, ventral and dorsal cortex and the rest fractions) was fresh-frozen on dry ice and stored at −80° C. for biochemical analysis (ELISA). Cerebellum was fresh-frozen and stored at −80° C. for optional future PK/other analysis.

Immunohistochemistry.

Twenty-µm-thick coronal sections were prepared with a cryostat and mounted on SuperFrost Plus glass slides from the fixed, cryoprotected and frozen hemispheres. Selected sections were used for immunohistochemical analyses. Plaque load and the degree of amyloid aggregates in cortical and hippocampal structures were analyzed with amyloid beta immunohistochemical staining.

From the adjacent sections, degree of microgliosis was analyzed with CD11b immunohistochemistry.

Aβ and CD11b Immunohistochemistry:

Briefly, tissue sections used in immunohistochemistry were thawed and air dried. After blocking the internal peroxidase activity and unspecific binding, and washes, sections were reacted overnight at RT with:

anti-Aβ (mouse anti-Aβ[4-10], the Genetics Company AB02, 1:20,000, clone W0-2)
anti-CD11b (rat anti-CD11b, AbD Serotec Inc. MCA711, 1:500)

Thereafter the sections were incubated with proper biotinylated secondary antibody and avidin-biotin complex (Vectastain Elite kit, Vector Laboratories, Burlingame, Calif.) for 2 h each. The peroxidase containing avidin-biotin complex was visualized using nickel-enhanced DAB as a substrate. Finally, the sections were rinsed, dehydrated, coverslipped and examined with a Leica 3000RB microscope.

Image Analysis.

Equally spaced coronal tissue sections along the antero-posterior axis of the hippocampus (3-4 tissue sections from each animal) were analyzed for immunostaining intensity by ImagePro Plus software. Images of immunoreactive staining were captured at defined light and filter settings in a bright-field microscope equipped with a color CCD-camera. The captured images of Aβ-immunoreactive plaque deposits and intraneuronal Aβ aggregates as well as CD11b immunoreactive images were converted to grayscale images, processed with a delineation function to sharpen edges to allow an accurate segmentation. The images were segmented with an auto-threshold command (ImageProPlus, MediaCybernetics). The results were expressed as area fraction (stained $area_{tot}$/measured $area_{tot}$, expressed in %) and presented as mean±SEM among the tissue sections analyzed from each individual transgenic mouse. Ventral cortex and dorsal hippocampus were analyzed from the coronal sections (at the AP level of dorsal hippocampus).

Insoluble and Soluble Amyloid Beta 1-42 ELISA.

Amyloid beta 1-42 ELISA analyses were applied to detect insoluble and soluble form of $A\beta_{1-42}$ in ventral cortex.

The ventral cortex tissue sample was homogenized and samples prepared according to the manufacturers detailed instructions (the Genetics Company, Switzerland, hAmyloid B42 Brain ELISA). Briefly the tissues were homogenized with a Dounce homogenizer (2×10 strokes on ice) in lysis buffer at a ratio of 1:10 (tissue weight:lysis buffer). Lysis buffer was Tris-buffered saline (TBS; 20 mM Tris-base and 137 mM NaCl, pH7.4) with protease inhibitors. The homogenate was centrifuged for 10 min at +4° C. with 13,000 rpm and the supernatant was divided in aliqouts and stored frozen at −20° C. prior to analyses (=Soluble AB).

The pellet was re-homogenized in cold 70% formic acid in distilled water, sonicated for 10 min, neutralized with 15× volume 1M Tris pH 7.4, and centrifuged for 10 min at +4° C. with 13,000 rpm. The supernatant was stored frozen at −20° C. (=Insoluble AB).

Figure 1B:
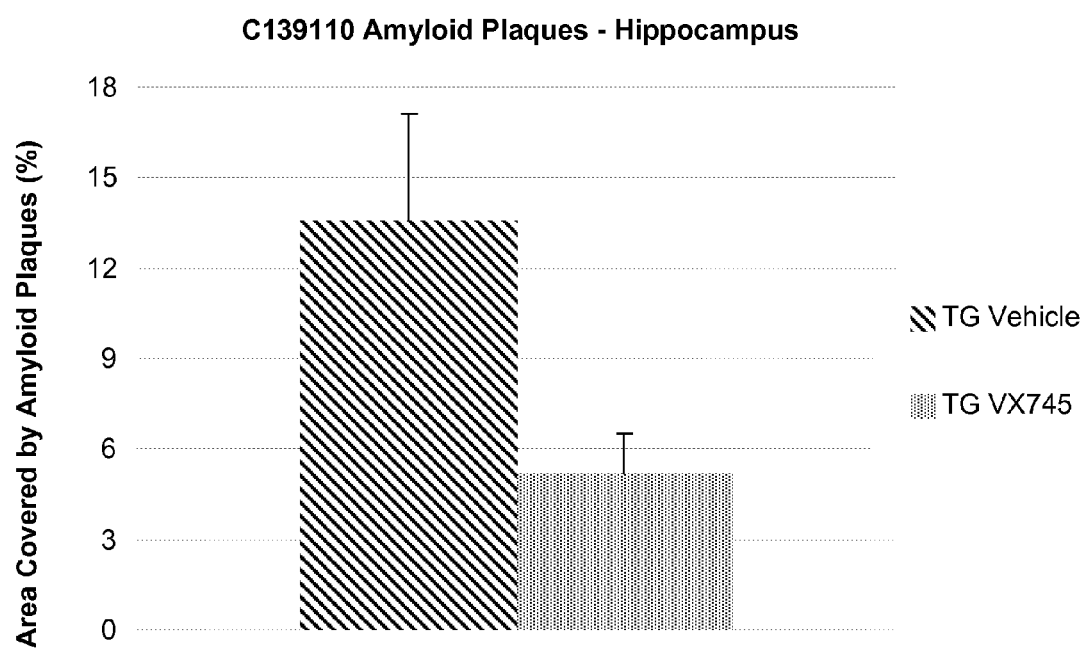

$A\beta_{1-42}$ levels in insoluble and soluble fractions of brain tissue samples were analyzed with ELISA using Amyloid Beta 1-42 ELISA kits (hAmyloid B42 Brain ELISAs, The Genetics Company, Switzerland) according to instructions of the manufacturer. Standard curve range was from 25 to 500 pg/ml. FIGS. 1A and 1B depict the area percentage of $A\beta_{1-42}$ amyloid plaques of transgenic mice following a two-week administration of VX-745 3 mg/kg BID. Of particular note, the present study was conducted on older mice (26 months of age). Other studies attempt to prevent amyloid plaque accumulation and are thus conducted on mice of about 4 and/or 8 months of age (see, for example, Zhu et al., *J. Neuroscience*, 31(4): 1355-136 (2011), incorporated herein by reference in its entirety). Tg2576 mice aged 26 months have elevated brain levels of soluble amyloid plaque by 6-8 months of age. The present experiments were designed to evaluate the amyloid plaque clearing ability of a p38 inhibitor (i.e., VX-745). Significantly, VX-745 showed a 32.5% decrease of amyloid plaque area in the cortex as compared with vehicle (mean 27.7% amyloid plaque area in control vs. mean 18.7% amyloid plaque area in VX-745-treated animals). VX-745 showed a 61.8% decrease of amyloid plaque area in the hippocampus as compared with vehicle (mean 13.6% amyloid plaque area in control vs. mean 5.2% amyloid plaque area in VX-745-treated animals).

IL-1β and TNF-α ELISA.

Figure 2:
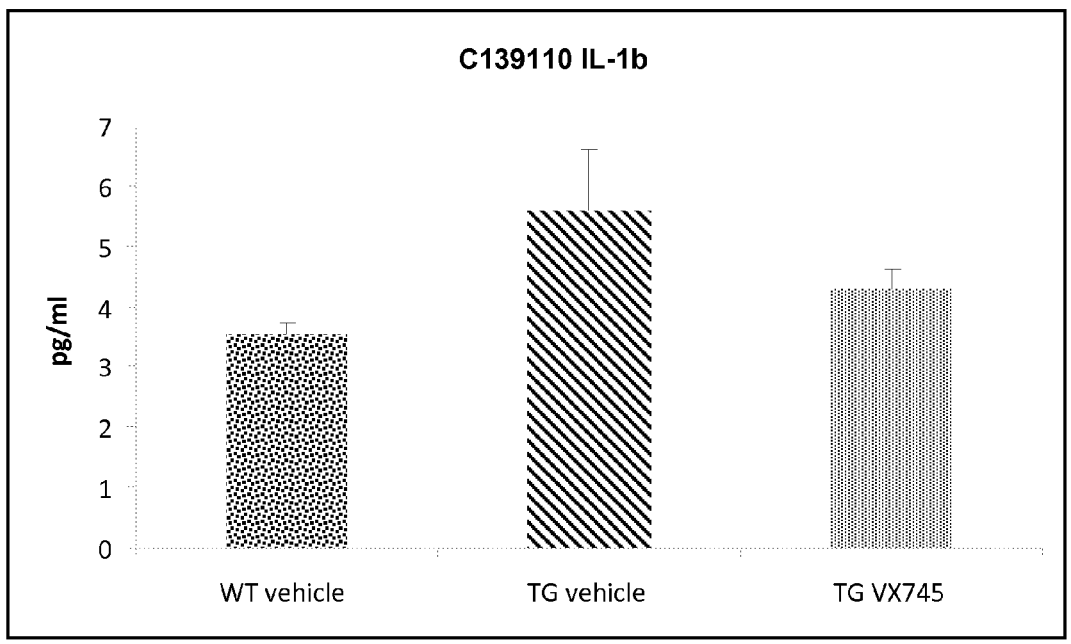
FIG. 2 summarizes the effects of VX-745 on IL-1β as compared to wild-type and vehicle controls.

IL-1β and TNF-α levels were analyzed from the soluble dorsal cortex brain tissue fraction with mouse IL-1β and TNF-α ELISA Kits (Quantikine M Cytokine mouse IL-1β and TNF-α ELISA kits, RND-Systems, MLB00 and MTA00, R&D Systems, MN, USA) according to instructions of the manufacturer. FIG. 2 depicts the IL-1β levels in transgenic mice following a two-week administration of VX-745 3 mg/kg BID. Increases in inflammation, particularly neuroinflammation, are known to trigger MAPT phosphorylation and aggregation through overexpression of IL-1. FIG. 2 depicts the IL-1β levels in treated mice vs. control and wild type mice. Notably, the VX-745-treated mice showed no increases in IL-1β levels when compared to the wild-type or control animals.

Statistical Analysis.

All data were presented as mean±standard deviation (SD) or standard error of mean (SEM), and differences were considered to be statistically significant at the $P<0.05$ level. Statistical analysis was performed using StatsDirect statistical software. Differences between group means were analyzed by using un-paired t-test.

I claim:

1. A method of treating a patient suffering from Alzheimer's Disease, the method comprising administering to the patient a pharmaceutical composition comprising VX-745.

2. The method of claim 1, wherein the patient has brain amyloid plaques.

3. The method of claim 1, wherein the pharmaceutical composition comprises VX-745 at a unit dose of less than 250 mg.

4. The method of claim 1, wherein the pharmaceutical composition is administered to the patient twice per day.

5. The method of claim 1, wherein the pharmaceutical composition is administered to the patient once per day.

6. The method of claim 1, wherein the pharmaceutical composition is formulated for oral administration.

* * * * *